United States Patent
Yagi et al.

(10) Patent No.: US 9,970,848 B2
(45) Date of Patent: May 15, 2018

(54) METHOD FOR EVALUATING STATE OF HORNY LAYER AND METHOD FOR EVALUATING HORNY LAYER IMPROVEMENT EFFECT OF COSMETIC PREPARATION

(71) Applicant: Shiseido Company, Ltd., Chuo-ku, Tokyo (JP)

(72) Inventors: Eiichiro Yagi, Kanagawa (JP); Ichiro Iwai, Kanagawa (JP)

(73) Assignee: Shiseido Company, Ltd., Tokyo (JP)

(*) Notice: Subject to any disclaimer, the term of this patent is extended or adjusted under 35 U.S.C. 154(b) by 382 days.

(21) Appl. No.: 14/761,386

(22) PCT Filed: Jan. 21, 2014

(86) PCT No.: PCT/JP2014/051110
§ 371 (c)(1),
(2) Date: Jul. 16, 2015

(87) PCT Pub. No.: WO2014/112643
PCT Pub. Date: Jul. 24, 2014

(65) Prior Publication Data
US 2015/0362412 A1 Dec. 17, 2015

(30) Foreign Application Priority Data
Jan. 21, 2013 (JP) .................. 2013-008590

(51) Int. Cl.
*G01N 1/30* (2006.01)
*A61Q 19/00* (2006.01)
(Continued)

(52) U.S. Cl.
CPC .............. *G01N 1/30* (2013.01); *A61B 5/442* (2013.01); *A61B 5/443* (2013.01); *A61B 5/4848* (2013.01);
(Continued)

(58) Field of Classification Search
CPC ...... G01N 1/30; G01N 33/5088; G01N 33/52; G01N 2001/302; A61B 5/442;
(Continued)

(56) References Cited

U.S. PATENT DOCUMENTS

2006/0216756 A1* 9/2006 Fujita ............... G01N 21/6428
435/7.2
2007/0179198 A1 8/2007 Iwai et al.
2010/0303872 A1 12/2010 Dumas et al.

FOREIGN PATENT DOCUMENTS

JP 2004-340935 A 12/2004
JP 2005-249672 A 9/2005
(Continued)

*Primary Examiner* — Navin Natnithithadha
(74) *Attorney, Agent, or Firm* — Foley & Lardner LLP

(57) ABSTRACT

The invention relates to providing a method for more conveniently evaluating stratum corneum condition. A stratum corneum sheet is contacted with a solution of a water-soluble dye, and the staining intensity or fluorescence intensity is measured to allow convenient evaluation of the stratum corneum condition. There is further provided a method for evaluating the ameliorating effect of a cosmetic or cosmetic treatment on the stratum corneum, by implementing the method for evaluating stratum corneum condition using a water-soluble dye according to the invention.

9 Claims, 6 Drawing Sheets

(51) Int. Cl.
  *G01N 33/52* (2006.01)
  *A61B 5/00* (2006.01)
  *A61K 8/49* (2006.01)
  *G01N 33/50* (2006.01)

(52) U.S. Cl.
  CPC .............. *A61K 8/498* (2013.01); *A61Q 19/00* (2013.01); *G01N 33/5088* (2013.01); *G01N 33/52* (2013.01); *A61K 2800/434* (2013.01); *G01N 2001/302* (2013.01)

(58) Field of Classification Search
  CPC ...... A61B 5/443; A61B 5/4848; A61K 8/498; A61K 2800/434; A61Q 19/00
  USPC .......................................................... 600/306
  See application file for complete search history.

(56) References Cited

FOREIGN PATENT DOCUMENTS

| | | |
|---|---|---|
| JP | 2006-349372 A | 12/2006 |
| JP | 2007-033201 A | 2/2007 |
| JP | 2007-263655 A | 10/2007 |
| JP | 2009-036555 A | 2/2009 |
| JP | 2011-164051 A | 8/2011 |
| JP | 2011-169655 A | 9/2011 |
| JP | 2012-202969 A | 10/2012 |

\* cited by examiner (A)

(B)

(A)

(B)

METHOD FOR EVALUATING STATE OF HORNY LAYER AND METHOD FOR EVALUATING HORNY LAYER IMPROVEMENT EFFECT OF COSMETIC PREPARATION

CROSS-REFERENCE TO RELATED APPLICATIONS

This application is a National Stage application of PCT/JP2014/051110, filed Jan. 21, 2014, which claims priority from Japanese application JP 2013-008590, filed Jan. 21, 2013.

The present invention relates to a method for evaluating the condition of the stratum corneum. The invention also relates to a method for evaluating the ameliorating effect on the stratum corneum by a cosmetic or cosmetic treatment.

BACKGROUND ART

When selecting a cosmetic it is extremely important to precisely determine the condition of the skin, and in order to maintain a more desirable skin condition it is necessary to select cosmetics and cosmetic methods suited for the particular skin condition. Evaluation of skin condition is carried out by measuring skin softness using a Reviscometer or Cutometer, by measurement of transepidermal water loss (TEWL), by measurement of skin physiology with a microscope, or by evaluation of the stratum corneum using a tape strip (NPLs 1, 2 and 3, and PTL 1). Of these, evaluation of the stratum corneum using a tape strip allows easy sampling and is considered effective for properly evaluating skin condition, and a method has been disclosed in which observation of the shapes, area and presence of nuclei in the cornified cells is also combined with observation of the stratum corneum stained with congo red that is capable of staining the β-sheet structure, to allow diagnosis of the softness of the skin (PTL 2).

Skin softness represented by the abundance of the β-sheet structure is one indicator of the stratum corneum condition, but in addition to softness, other various properties such as transparency, stratum corneum intercellular lipid structure and stratum corneum barrier function also indicate the stratum corneum condition. However, insufficient research has been conducted toward convenient measurement of such information based on tape-stripped stratum corneum, and no method has been established to allow convenient diagnosis of skin roughened state.

CITATION LIST

Patent Literature

[PTL 1] Japanese Unexamined Patent Publication No. 2007-033201
[PTL 2] Japanese Unexamined Patent Publication No. 2007-263655

Non-Patent Literature

[NPL 1] Osanai, O. et al.: Anti-aging series: Cutting edge research for skin anti-aging, p. 150-p. 161
[NPL 2] Takahashi, M. et al.: Anti-aging series: Cutting edge research for skin anti-aging, p. 114-p. 133
[NPL 3] Integral, Co., Ltd.: Fragrance Journal, 35(2), p. 67 to p. 69(2007)

DISCLOSURE OF THE INVENTION

Problems to be Solved by the Invention

An object of the invention is to provide a method for more conveniently evaluating stratum corneum condition. It is another object of the invention to provide a method for evaluating candidate cosmetics or cosmetic treatments in regard to their ameliorating effects on the stratum corneum, using the method for conveniently evaluating stratum corneum condition.

Means for Solving the Problems

It is known that in ravaged stratum corneum, the stratum corneum transparency is reduced, the barrier function is reduced and the intercellular lipids are disordered. While it is possible to evaluate the stratum corneum condition using these indicators, measurement of the indicators has required special equipment for each. The present inventors therefore conducted diligent research with the aim of providing a method of more conveniently evaluating stratum corneum condition. As a result, it was found that when the stratum corneum sheet is stained with fluorescein or rose bengal the staining intensity is higher in ravaged stratum corneum (FIG. 1 and FIG. 2), and that staining with fluorescein or rose bengal provides excellent sensitivity for discrimination of the state even of skin that appears at first glance to be healthy (FIG. 3), allowing evaluation of the stratum corneum condition of the stratum corneum sheet. Furthermore, by using the method of evaluating stratum corneum condition, we provided a method of evaluating candidate cosmetics or cosmetic treatments in regard to their ameliorating effect on the stratum corneum.

More specifically, the present invention relates to the following inventions.

[1] A method for evaluating stratum corneum condition, comprising:
contacting a stratum corneum sheet with an aqueous solution of a dye selected from the group consisting of fluorescein, rose bengal and their salts,
rinsing the dye, and
measuring the staining intensity of the dye in the stratum corneum sheet.

[2] The method according to [1] above, wherein the evaluation of the stratum corneum condition is evaluation of stratum corneum transparency, stratum corneum intercellular lipid structure and stratum corneum moisture content.

[3] The method according to [1] or [2] above, wherein the evaluation is conducted based on comparison with the staining intensity from a prepared sample, or comparison with a color chart.

[4] The method according to any one of [1] to [3] above, wherein the stratum corneum sheet is a stratum corneum sheet prepared by tape stripping.

[5] A method for evaluating a candidate cosmetic for its ameliorating effect on the stratum corneum, the method comprising:
applying the candidate cosmetic to a stratum corneum sheet,
drying the stratum corneum sheet,
contacting the stratum corneum sheet with an aqueous solution of a dye selected from the group consisting of fluorescein, rose bengal and their salts,
rinsing the dye, and
measuring the staining intensity of the dye in the stratum corneum sheet.

[6] The method according to [5] above, wherein the stratum corneum sheet is a cultured stratum corneum sheet.

[7] A method for evaluating a cosmetic treatment in regard to its ameliorating effect on the stratum corneum, the method comprising:

contacting a prepared stratum corneum sheet, taken after cosmetic treatment of skin, with an aqueous solution of a dye selected from the group consisting of fluorescein, rose bengal and their salts, rinsing the dye, and measuring the staining intensity or fluorescence intensity of the dye in the prepared stratum corneum sheet.

[8] The method according to [7] above, wherein the evaluation is based on dye staining of a stratum corneum sheet obtained by tape stripping before cosmetic treatment, and comparing the fluorescence intensity of the stratum corneum sheet before and after cosmetic treatment.

[9] The method according to [8] above, wherein the cosmetic treatment is application of a cosmetic, application of steam, or massaging.

Effect of the Invention

According to the present invention it is possible to evaluate stratum corneum condition in a stratum corneum sheet using a dye selected from the group consisting of fluorescein, rose bengal and their salts. By allowing evaluation of stratum corneum condition, it is possible to confirm an ameliorating effect on the stratum corneum by evaluating the stratum corneum condition before and after application of a candidate cosmetic or cosmetic treatment.

BEST MODE FOR CARRYING OUT THE INVENTION

Figure 1:
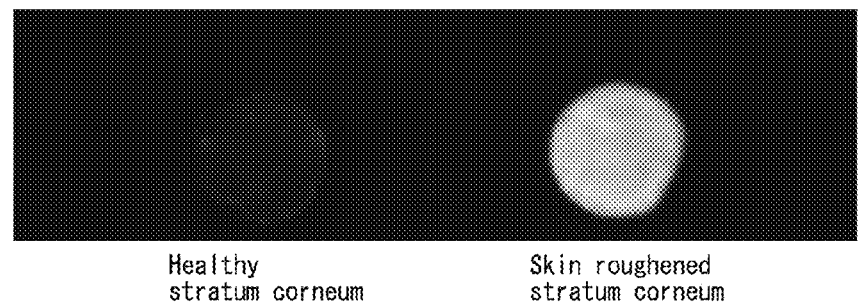
FIG. 1 shows images taken upon fluorescein staining of a healthy stratum corneum model obtained by slowly drying a cultured stratum corneum sheet that had been wetted with water, and a skin roughened stratum corneum model obtained by freeze-drying.

The invention relates to a method for evaluating stratum corneum condition, comprising a step of contacting a stratum corneum sheet with an aqueous solution of a dye selected from the group consisting of fluorescein, rose bengal and their salts, a step of rinsing the dye, and a step of measuring the staining intensity of the dye in the stratum corneum sheet. The stratum corneum condition can be represented by at least one factor selected from the group consisting of stratum corneum transparency, degree of stratum corneum intercellular lipid structuralization and stratum corneum moisture content, or any desired combination thereof. The invention is based on the discovery that when a stratum corneum sheet has been stained with a dye selected from the group consisting of fluorescein, rose bengal and their salts the staining intensity serves as an indicator of the stratum corneum condition, or in other words, of at least one factor selected from the group consisting of stratum corneum transparency, stratum corneum intercellular lipid structuralization degree and stratum corneum moisture content, or any desired combination thereof. Therefore, the stratum corneum condition can be evaluated according to the staining intensity of the stratum corneum sheet, with more intense staining being evaluated as a poorer stratum corneum condition and a rougher state, and judged as having lower stratum corneum transparency, a more disordered stratum corneum intercellular lipid structure and reduced stratum corneum moisture content. Evaluation of the stratum corneum condition can be accomplished by comparison with a color chart or staining intensity reference value, or comparison with the staining intensity of a reference sample. The reference sample may be, for example, a stratum corneum sheet in which skin roughening has been induced, prepared by coating a healthy stratum corneum sheet with a dilution series of a skin roughening inducer such as SDS and incubating for a fixed period, or it may be a stratum corneum sheet in which skin roughening has been induced, prepared by coating a fixed concentration of a skin roughening inducer-containing solution and incubating it in periods over time.

Throughout the present specification, a "stratum corneum sheet" may be any one that contains stratum corneum, and it is a stratum corneum sheet prepared using a method such as tape stripping from live skin (hereunder referred to as "prepared stratum corneum sheet"), or a stratum corneum sheet obtained from cell culturing (hereunder referred to as "cultured stratum corneum sheet"). The stratum corneum sheet to be used in the method for evaluating stratum corneum condition or the method for evaluating a cosmetic treatment is preferably a prepared stratum corneum sheet, and more preferably it is a prepared stratum corneum sheet sampled by tape stripping. A prepared stratum corneum sheet sampled by tape stripping may also be simply stratum corneum or stratum corneum cells prepared by tape stripping. The stratum corneum sheet to be used in the method for evaluating a candidate cosmetic is preferably a cultured stratum corneum sheet from the viewpoint of large-scale and uniform screening. A cultured stratum corneum sheet can be sampled by three-dimensional model culturing of skin, but it may also be a stratum corneum sheet sampled from commercially available cultured epidermis, such as cultured epidermis marketed by Japan Tissue Engineering Co., Ltd.

It has been found by the present inventors that when a stratum corneum sheet is wetted with solution and rapidly dried, the stratum corneum transparency is reduced, the barrier function is reduced and the intercellular lipid structure is disturbed (Japanese Patent Application No. 2011-283045), and a rapidly dried stratum corneum sheet can be used as a model of roughened stratum corneum. The present invention is based on the finding that when a stratum corneum sheet, as a skin roughening model that has been wetted with a solution and then rapidly dried, is stained with a water-soluble dye, the staining intensity is significantly high, and the staining intensity serves as an indicator of skin roughening, or in other words, of stratum corneum transparency, barrier function and intercellular lipid structure.

As used herein, a dye may be any desired dye that can be used for evaluation of stratum corneum condition, and any natural dye, synthetic dye or fluorescent dye may be used. A fluorescent dye is a dye that emits fluorescence, where "fluorescence" refers to light of a specific wavelength emitted from a substance that has been excited by electromagnetic waves. A dye to be used for evaluation of stratum corneum condition according to the invention is thought to powerfully stain skin-roughened stratum corneum upon its dissolution in water and permeation into a structure that is susceptible to infiltration of water, such as the cells of the stratum corneum that have low barrier function due to skin roughening, but it is not our intention to limit it to this mechanism. On the other hand, it is known that dyes such as congo red stain keratin fibers despite their water solubility (PTL 2), and thus cannot be used for evaluation of stratum corneum condition. When the staining specificity thus depends on the type of dye it is not possible to evaluate stratum corneum condition, and therefore low staining specificity is desired. Furthermore, from the viewpoint of using live stratum corneum, high safety is naturally another desirable property. Dyes to be used for evaluation of stratum corneum condition according to the invention must have safety, water-solubility and low staining specificity, and from the viewpoint of satisfying one or more of these properties, examples of fluorescent dyes include fluorescein and its salts, as well as derivatives of the same, and examples of dyes other than fluorescent dyes include rose bengal and its salts, as well as derivatives of the same. As salts of dyes there may be used any desired salts, and from the viewpoint of satisfying one or more of the properties of safety, water-solubility and low staining specificity, it is preferred to use sodium salts, potassium salts, calcium salts and the like.

According to the invention, the step of contacting the stratum corneum sheet with the dye aqueous solution may be carried out by any desired means so long as the stratum corneum sheet and the dye aqueous solution are contacted, and for example, it may be carried out by immersing the stratum corneum sheet in the dye aqueous solution, or by dropping or coating the dye aqueous solution onto the stratum corneum sheet.

The step of rinsing the water-soluble dye will usually be a step of washing off the dye with a solvent such as water, but there is no limitation to the solvent, and a solution such as an aqueous solution may be used instead. The rinsing may be carried out any desired number of times, and preferably 1 to 3 times, or it may be carried out a greater number of times.

Measurement of the staining intensity can usually be accomplished by observing the dye-stained stratum corneum sheet with an optical microscope or the like, and using commercially available image processing software for digitization of the observed image. When staining is accomplished using a fluorescent dye, on the other hand, the staining intensity can be measured by measuring the fluorescent brightness. Measurement of the fluorescent brightness can usually be accomplished by irradiating the fluorescent dye-stained stratum corneum sheet with electromagnetic waves that include ultraviolet rays and measuring the emitted fluorescence, with the measurement being carried out using a fluorescence measuring instrument such as a luminometer or fluorescent microscope. On the other hand, since ultraviolet rays are usually included in sunlight or fluorescent lamp light and therefore fluorescence can be confirmed even under visible light, the fluorescence intensity may be classified visually under visible light, but preferably an ultraviolet ray generator such as a black light is used to confirm the fluorescence. When the fluorescence intensity is to be measured using a fluorescent microscope, since there will be sections that emit fluorescence and sections that do not emit fluorescence, it is necessary to measure the fluorescent light quantity with random selection of a plurality of visual fields, and such processing can be carried out using image processing software provided with the fluorescent microscope.

According to another mode of the invention, the invention relates to a method for evaluating a candidate cosmetic in regard to its ameliorating effect on the stratum corneum, by applying the method for evaluating stratum corneum condition. More specifically, the method for evaluating a candidate cosmetic comprises the following steps: a step of applying the candidate cosmetic to a stratum corneum sheet, a step of drying the stratum corneum sheet, a step of contacting the stratum corneum sheet with an aqueous solution of a dye selected from the group consisting of fluorescein, rose bengal and their salts, a step of rinsing the dye, and a step of measuring the staining intensity of the dye in the stratum corneum sheet. This evaluation method allows evaluative screening of products, based on whether or not different candidate cosmetics have ameliorating effects on the stratum corneum. Also, by setting the drying conditions, it may be judged whether or not a cosmetic is suited for use environments, thus facilitating product development.

As used herein, "ameliorating effect on the stratum corneum" means an improvement in stratum corneum transparency, an ordering of stratum corneum intercellular lipid structure or a reduction in stratum corneum moisture content, or a combination of two or more thereof, for the stratum corneum. By judging whether or not a candidate cosmetic has such an ameliorating effect on the stratum corneum, it is possible to judge whether or not the candidate cosmetic contributes to more beautiful, healthy skin.

The step of applying a candidate cosmetic to the stratum corneum sheet in the method for evaluating a candidate cosmetic may be carried out by immersing the stratum corneum sheet in the candidate cosmetic, or it may be accomplished by a method of external application on the stratum corneum sheet, such as dropping or coating, or attachment or packing, of the candidate cosmetic.

The conditions for the stratum corneum sheet drying step in the method for evaluating the candidate cosmetic may be selected as appropriate for the environment in which the candidate cosmetic is to be used. The present inventors have found that the stratum corneum condition changes throughout the process of drying of water-wetted stratum corneum (Japanese Patent Application No. 2011-283045), and it is thought that slowly drying wetted stratum corneum improves stratum corneum transparency and orders intercellular lipids. Here, the drying conditions may be selected according to the environment, and for example, by selecting low humidity conditions for cosmetics that are expected to be marketed in dry regions, or high humidity and high-temperature conditions for cosmetics that are expected to be marketed in high temperature, high humidity regions, it is possible to select cosmetics having ameliorating effects on the stratum corneum in such regions. Furthermore, the environment in which a cosmetic is to be used changes significantly depending on the season of the marketing region. Thus, according to a more preferred embodiment of the invention, it is possible to evaluate whether a cosmetic is suited for different seasons in the marketing region, for example, for the dry season or rainy season, or for the spring, summer, fall or winter seasons. For screening of candidate cosmetics having more excellent ameliorating effects on the stratum corneum, more severe conditions may be selected, such as high-temperature and low humidity conditions, or the temperature may be selected in consideration of body temperature. The range of temperature selection may be, for example, 10° C. to 45° C., and more preferably a temperature range selected from among 10° C., 15° C. and 20° C. for the lower limit and 20° C., 25° C., 30° C., 35° C., 37° C. and 40° C. for the upper limit. The humidity selected may be any desired humidity, and for example, it may be selected to be 50% or greater, 60% or greater, 70% or greater, 80% or greater, 90% or greater, 95% or greater, or 100%. There are no particular restrictions on the drying time, which may be selected so as to be a time sufficient for disappearance of the candidate cosmetic liquid, and a fixed time, such as 1 minute, 2 minutes, 5 minutes, 10 minutes, 15 minutes, 30 minutes, 1 hour, 2 hours, 3 hours or 4 hours, may be selected as appropriate.

According to another mode of the invention, the invention relates to a method for evaluating a cosmetic treatment in regard to its ameliorating effect on the stratum corneum, by applying the method for evaluating stratum corneum condition. More specifically, the method for evaluating a cosmetic treatment is a method for evaluating a cosmetic treatment in regard to its ameliorating effect on the stratum corneum, the method comprising the following steps: a step of contacting a stratum corneum sheet, taken by tape stripping after cosmetic treatment of skin, with a dye selected from the group consisting of fluorescein, rose bengal and their salts, a step of rinsing the dye, and a step of measuring the staining intensity of the dye in the stratum corneum sheet. This evaluation method allows evaluation of whether or not an applied cosmetic treatment contributes to stratum corneum condition, and particularly stratum corneum transparency, ordering of the intercellular lipid structure, and/or reduction in stratum corneum moisture content. Preferably, the evaluation is carried out by comparison between the staining intensity of a stratum corneum sheet obtained by tape stripping before cosmetic treatment and the staining intensity of a stratum corneum sheet obtained by tape stripping after cosmetic treatment. In this case, with staining intensity reduction, and particularly a reduction of preferably 5% or greater, more preferably 10% or greater and even more preferably 20% or greater, it may be judged that the cosmetic treatment has an ameliorating effect on the stratum corneum.

There are no particular restrictions on the cosmetic treatment, and examples include various treatments considered to be effective for body esthetics, such as coating with a cosmetic, application of massage, application of steam and the like. The cosmetic treatment may be a single treatment, or it may be continuous treatment conducted over several days or several weeks. The cosmetic treatment may be personal treatment, conducted in a beauty parlor, cosmetic retail store, esthetic salon or the like, and the method for evaluating the cosmetic treatment may also be conducted in a beauty parlor, cosmetic retail store, esthetic salon or the like.

As used herein, "cosmetic" means a cosmetic to be applied onto skin, such as cosmetic water, latex, essence, cream or foundation, for example, with no particular limitation to these. That is, a cosmetic according to the invention includes all substances that are not directly for the purpose of improving skin but are to be applied onto skin, and for example, it includes sunscreens, insect repellents, allopecia agents, hair restorers, shaving lotions and after shave lotions. The components in the cosmetic may include water or alcohols such as ethanol, glycerin or polyethylene glycol as bases, amino acids such as glycine, betaine, Na pyrrolidone carboxylate or saccharides such as fructose, maltitol, mannitol or trehalose, as humectants, hyaluronic acid, collagen, ceramide or the like as active ingredients, sodium citrate, citric acid or sodium lactate as diluting agents, and benzoic acid salts or sorbic acid as antiseptic agents, with no particular limitation to these.

As used herein, "candidate cosmetic" refers to a cosmetic that is to be examined in regard to its corneum-ameliorating effect, and it includes cosmetics marketed as products, as well as cosmetics that are in the development stage, and also solutions selected for use in cosmetics in the course of cosmetic development. For example, in order to examine the corneum-ameliorating effect of a substance to be used in a cosmetic, the "cosmetic" may be an aqueous solution containing the substance alone. Aqueous solutions of AQUAIN-POOL® and erythritol were used throughout the examples in the present specification, but there is no limitation to these aqueous solutions, and there may be used components included as saccharides, polyhydric alcohols, amino acids, organic acids, humectants such as trehalose, mannitol, glycerin, polyethylene glycol, hyaluronic acid, chondroitin sulfate and glucosamine, thickeners, or buffering agents, or optional aqueous solutions of active ingredients, while there may also be used solutions containing solvents other than water. POE(14) POP(7) dimethyl ether is a polyoxyethylene-polyoxypropylene random copolymer dimethyl ether, and because it contains a substance that can dissolve in oils as well as water, it is a substance that can be used as an aqueous base or an oil base. The general formula for POE POP dimethyl ether is as follows:

[Chemical Formula 1]

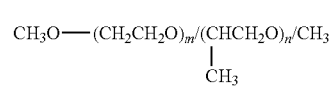

The POE (14) POP(7) dimethyl ether used for the invention is one wherein m=14 and n=7, although m and n may be any desired integers.

According to the invention, the skin barrier function is evaluated by transepidermal water loss (TEWL). The TEWL is the amount of transpiration of moisture through the stratum corneum, a lower TEWL indicating higher stratum corneum skin barrier function and higher TEWL indicating lower stratum corneum skin barrier function. The relationship between skin barrier function and skin roughening is described in PTL 2.

The present invention will now be explained in greater detail with reference to concrete examples, with the understanding that the invention is not meant to be limited to these examples.

EXAMPLES

Example 1

Fluorescein Staining of Cultured Stratum Corneum Sheet

A cultured stratum corneum sheet was prepared from LabCyte EPI-MODEL three-dimensional culture skin (product of Japan Tissue Engineering Co., Ltd.), and after wetting the cultured stratum corneum sheet with water, a constant temperature zone (MTH-2200) was used for 8 hours of incubation of the cultured stratum corneum sheet at 60% humidity, 32° C. for drying, to prepare a healthy stratum corneum model. After wetting with water, a freeze-drying apparatus (VD-80, product of Taitec) was used for freezing to −20° C., and freeze-drying was carried out for 2 hours with the same apparatus to prepare a skin roughened stratum corneum model. The dried cultured stratum corneum sheet was immersed for 5 minutes in a 0.2 w/v % uranin (fluorescein/sodium) solution (product of Wako Pure Chemical Industries, Ltd.), and after rinsing, it was irradiated with blue light (Light therapy treatment by Tanda Professional Clear), and a photograph was taken (FIG. 1). The obtained image was represented extracting the green component using image processing software (Image J).

Example 2

Figure 2:
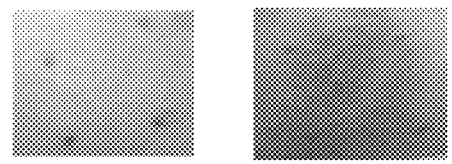
FIG. 2 shows results after fluorescein staining of a skin-roughened stratum corneum sheet obtained by tape stripping from skin in which roughening had been induced by 10% SDS treatment, and a healthy stratum corneum sheet obtained from skin at a site not subjected to SDS treatment. Shown are the states of the skin (FIG. 2A) and a graph representing fluorescent brightness upon fluorescein staining (FIG. 2B).
Figure 2:
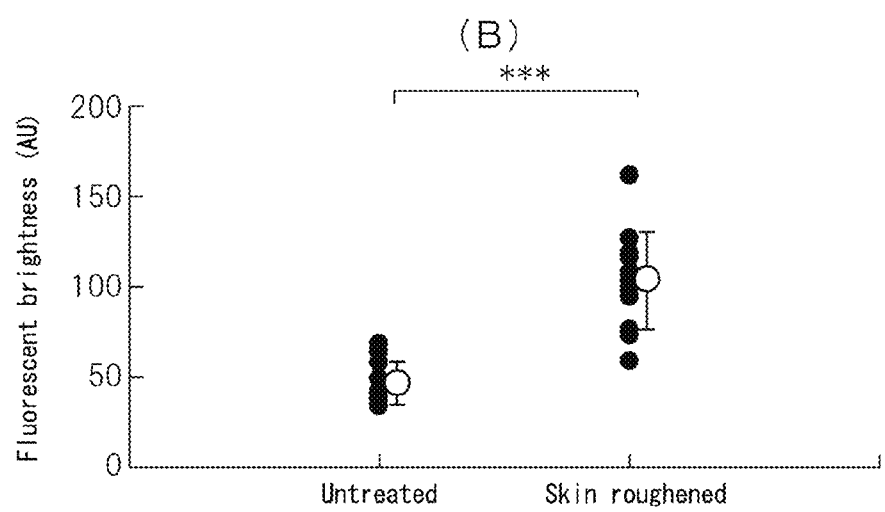

Fluorescein Staining of Stratum Corneum Sheet, Tape Stripped from Skin Roughened by SDS Coating The brachial flexor region was coated by occlusion for 1 hour with a 2.5×2.5 cm nonwoven fabric immersed in 10% sodium dodecyl sulfate (SDS), for 2 days, eliciting skin roughening (FIG. 2A). After 7 days, the stratum corneum sheet was released by tape stripping and affixed to a glass slide. Also, a section not treated with SDS was released in the same manner and affixed onto a glass slide. Each affixed stratum corneum sheet was immersed for 5 minutes in a 0.2 w/v % uranin solution (Wako Pure Chemical Industries, Ltd.), and after rinsing, the fluorescent brightness was observed with a fluorescent microscope (BX51 by Olympus Corp.) and an image was taken. The taken image was corrected for distortion and digitized using analysis software, and the fluorescent brightness was calculated. FIG. 2B shows a graph in which data for 12 visual fields are averaged. The fluorescent brightness was significantly higher with the stratum corneum sheet taken from the skin roughened section ($p<0.001$).

Example 3

Figure 3:
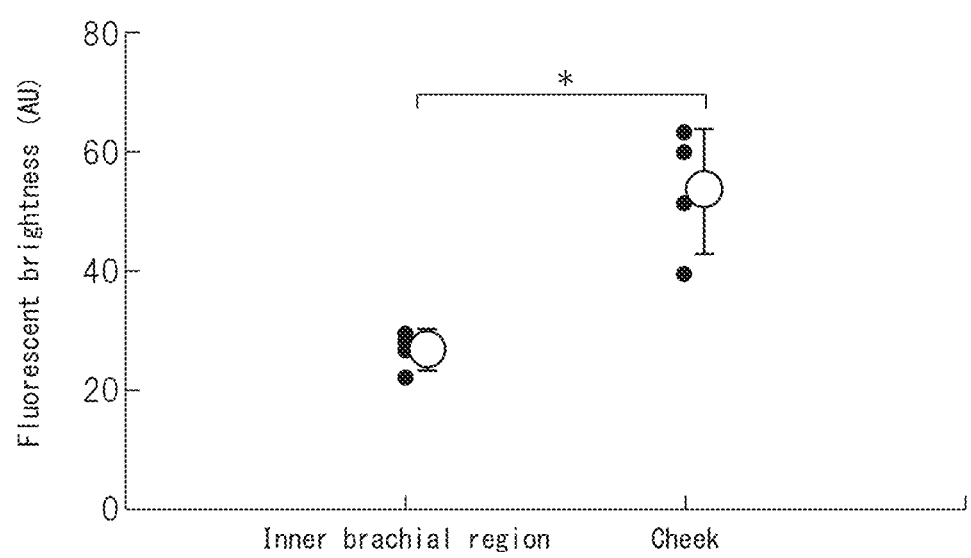
FIG. 3 shows a graph representing fluorescent brightness after fluorescein staining of a stratum corneum sheet obtained by tape stripping from skin on the inner brachial region, and a stratum corneum sheet obtained from cheek skin.

Fluorescein Staining of Stratum Corneum Sheets Obtained by Tape Stripping from Inner Brachial Region and Cheek Stratum corneum sheets were released by tape stripping from the buccal regions and inner brachial regions of four males, and affixed to glass slides. Each of these was immersed for 5 minutes in a 0.2 w/v % uranin solution (Wako Pure Chemical Industries, Ltd.), and after rinsing, the fluorescent brightness was observed with a fluorescent microscope (BX51 by Olympus Corp.) and an image was taken. The taken image was corrected for distortion and digitized using analysis software, and the fluorescent brightness was calculated. FIG. 3 shows a graph in which data for each of 6 visual fields are averaged. None of the buccal regions or inner brachial regions exhibited skin roughening, but presumably the cheeks that are exposed to external air and ultraviolet rays during daily living activities undergo more deterioration in the stratum corneum condition than the inner brachial region. The stratum corneum sheets taken from the buccal region had significantly higher fluorescent brightness than those from the inner brachial region ($p<0.05$), thus demonstrating that the method of the invention allows diagnosis not only of visible skin roughened states but also of the state of non-visible levels of skin roughening.

Example 4

Fluorescein Staining of Human Stratum Corneum Sheet Obtained from Skin Wetted with Water In Vivo and then Dried at Low Humidity (10%) or High Humidity (90%)

Figure 4:
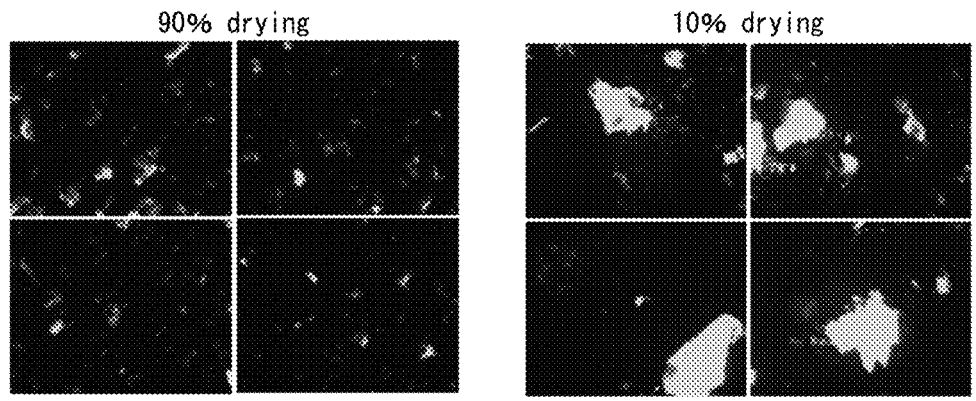
FIG. 4 shows an image taken upon fluorescein staining of a stratum corneum sheet obtained by wetting of skin in vivo followed by drying to low humidity (10%) or high humidity (90%), and then tape stripping (FIG. 4A), and a graph representing fluorescent brightness measured in 12 visual fields selected within the image (FIG. 4B).
Figure 4:
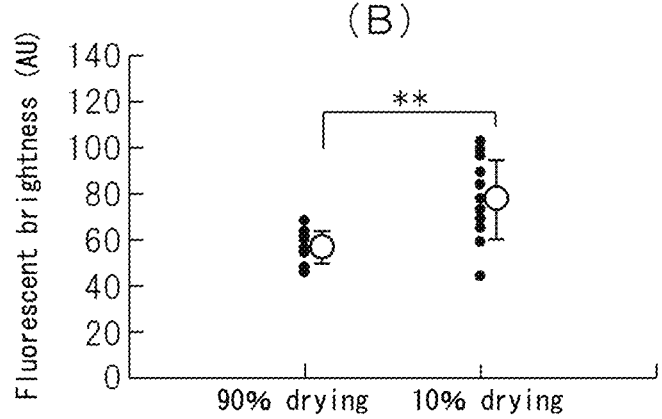

A 2.5×2.5 cm water-wetted nonwoven fabric was coated by occlusion for 2 hours on the brachial flexor region (both arms). The nonwoven fabric was removed and set in a thermostatic chamber at 10% humidity, 22° C. temperature, and one arm was inserted, from the shoulder, into a vinyl bag containing supersaturated potassium nitrate, and allowed to stand for 1 hour. The humidity of the interior of the vinyl bag containing the supersaturated potassium nitrate was approximately 90%. After returning it to the laboratory (25% humidity) and allowing it to stand for 1 hour, the stratum corneum sheet was released from the treated sections of both arms with stratum corneum release tape and affixed to a glass slide. Each affixed stratum corneum sheet was immersed for 5 minutes in a 0.2 w/v % uranin solution (Wako Pure Chemical Industries, Ltd.), and after rinsing, the fluorescent brightness was observed with a fluorescent microscope (BX51 by Olympus Corp.) and an image was taken (FIG. 4A). The taken image was corrected for distortion and digitized using analysis software, and the fluorescent brightness was calculated. FIG. 4B shows a graph in which data for each of 12 visual fields are averaged. The skin stratum corneum dried at low humidity (10%) had significantly higher fluorescent brightness than the skin stratum corneum dried at high humidity (90%). ($P<0.01$)

Example 5

Figure 5:
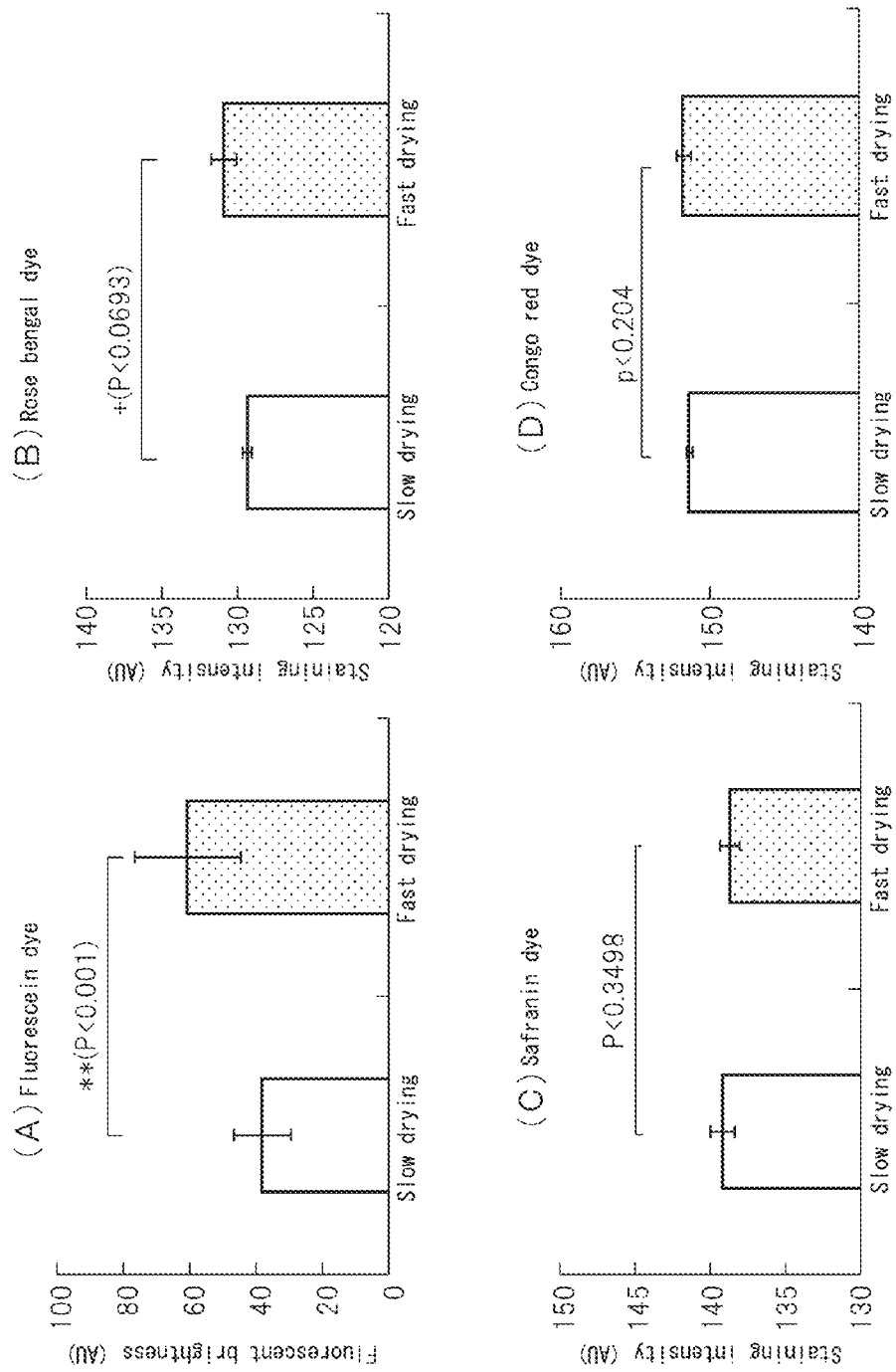
FIG. 5 is a set of graphs showing staining intensity obtained using different dyes for staining of stratum corneum taken by tape stripping from skin, that was wetted with water and slowly dried to 90% humidity, and the same rapidly dried using silica gel. The dyes used were (A) fluorescein, (B) rose bengal, (C) safranin and (D) congo red.

Staining of Stratum Corneum Sheet Obtained by Tape Stripping, after Water Wetting, and Dried at 90% Humidity or Dried Using Silica Gel Two stratum corneum sheets were each obtained from the forearm flexor region using stratum corneum release tape, and affixed to a glass slide. After immersing these in water for 1 hour, one was dried for 2 hours in a sealed container containing supersaturated potassium nitrate. The humidity during this time was approximately 90%. The other sheet was dried for 2 hours in a sealed container containing dried silica gel. The humidity during this time was approximately 0%. Each of the stratum corneum sheets was immersed for 5 minutes in a 0.2 w/v % uranin solution (Wako Pure Chemical Industries, Ltd.), and after rinsing, the fluorescent brightness was observed with a fluorescent microscope (BX51 by Olympus Corp.) and an image was taken. The taken image was corrected for distortion and digitized using analysis software, and the fluorescent brightness was calculated. FIG. 5A shows a graph in which data for each of 12 visual fields are averaged. The stratum corneum sheet obtained by tape stripping can be immersed in water and rapidly dried using silica gel to prepare a skin-roughened stratum corneum sheet model, in which case changes in fluorescent brightness can be measured. The stratum corneum dried with silica gel has significantly higher fluorescent brightness than the stratum corneum dried at high humidity ($P<0.001$).

The same experiment was also conducted using different dyes, a 0.2 w/v % rose bengal solution (Wako Pure Chemical Industries, Ltd.), a 0.2 w/v % saffron aqueous solution (Wako Pure Chemical Industries, Ltd.) and a 0.2 w/v % congo red aqueous solution (Wako Pure Chemical Industries, Ltd.). The stratum corneum sheets prepared by this method were immersed for 5 minutes in the respective dye aqueous solutions, and after rinsing, they were observed using an optical microscope (BX40 by Olympus Corp.) and the images were inputted. The inputted images were digitized with image analysis software and the color intensities calculated. FIGS. 5B), C) and D) show graphs in which data for each of 12 visual fields are averaged. With rose bengal staining, the stratum corneum dried with silica gel tended to have higher staining intensity than the stratum corneum dried at high humidity. ($p<0.1$) With safranin staining and congo red staining, on the other hand, it was not possible to evaluate any difference due to drying.

Example 6

Screening of Candidate Cosmetics for Ameliorating Effect on the Stratum Corneum

Figure 6:
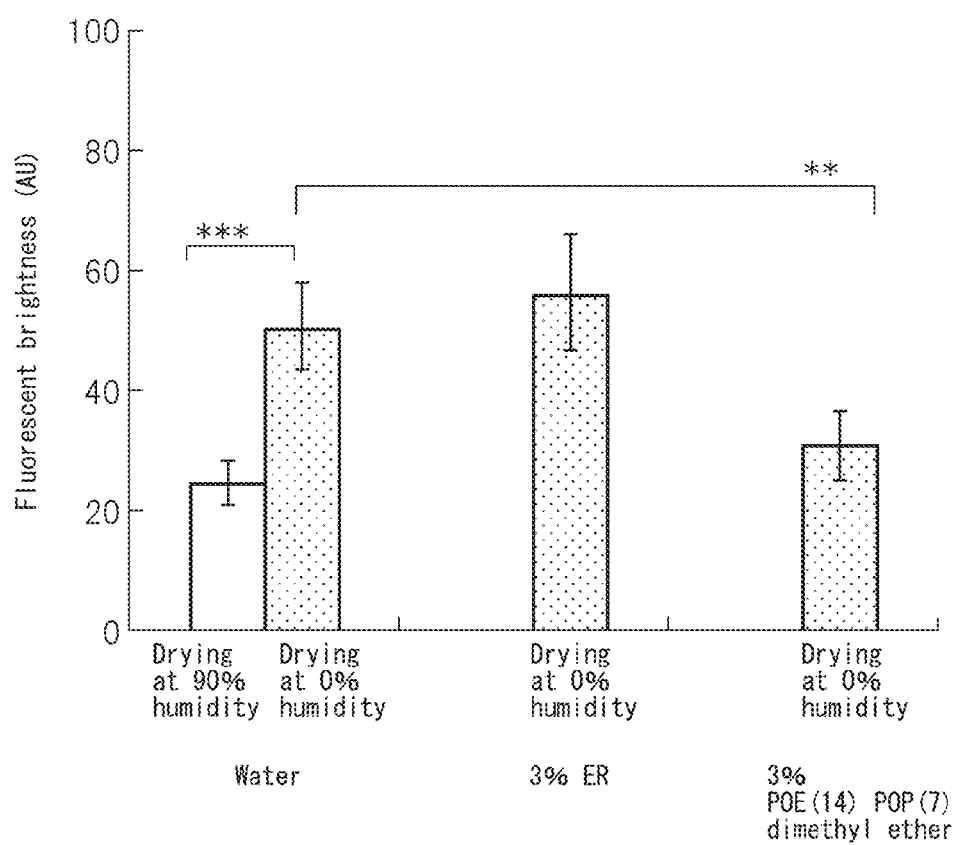
FIG. 6 shows a graph representing fluorescent brightness with fluorescein staining of a stratum corneum sheet after immersion in water, 3% erythritol (ER) and 3% POE(14) POP(7) dimethyl ether, and then drying at 0% humidity in a sealed container containing silica gel. The results with drying at 90% humidity in water are also shown for comparison.

Stratum corneum sheets obtained from the forearm flexor region using stratum corneum release tape were affixed to glass slides, and each affixed stratum corneum sheet was immersed for one hour in water (two sheets) as a control and in a 3% erythritol aqueous solution (ER) and a 3% AQUAINPOOL 1407 aqueous solution (AQ), as candidate cosmetics. Next, one of the water-wetted stratum corneum sheets was dried at 0% humidity, room temperature, while the other was dried for 2 hours at 90% humidity, room temperature. The stratum corneum sheets wetted with ER and AQ were dried for 2 hours at 0% humidity, room temperature. Each of the stratum corneum sheets was immersed for 5 minutes in a 0.2 w/v % uranin solution (Wako Pure Chemical Industries, Ltd.), and after rinsing, the fluorescent brightness was observed with a fluorescent microscope (BX51 by Olympus Corp.) and an image was taken. The taken image was corrected for distortion and digitized using analysis software, and the fluorescent brightness was calculated. FIG. 6 shows a graph in which data for each of 12 visual fields are averaged. With the ER-wetted stratum corneum sheet, the fluorescent brightness was about the same as with the water-wetted stratum corneum sheet (dried at 0% humidity), while with the AQ-wetted stratum corneum sheet the fluorescent brightness was significantly lower than with the water-wetted stratum corneum sheet (dried at 0% humidity), and the fluorescent brightness was close to the value of the stratum corneum sheet that had been wetted with water and slowly dried at 90% humidity. This experiment demonstrated that a 3% AQUAINPOOL 1407 aqueous solution has an ameliorating effect on the stratum corneum, indicating that this experimental system allows screening of candidate cosmetics.

Example 7

Figure 7:
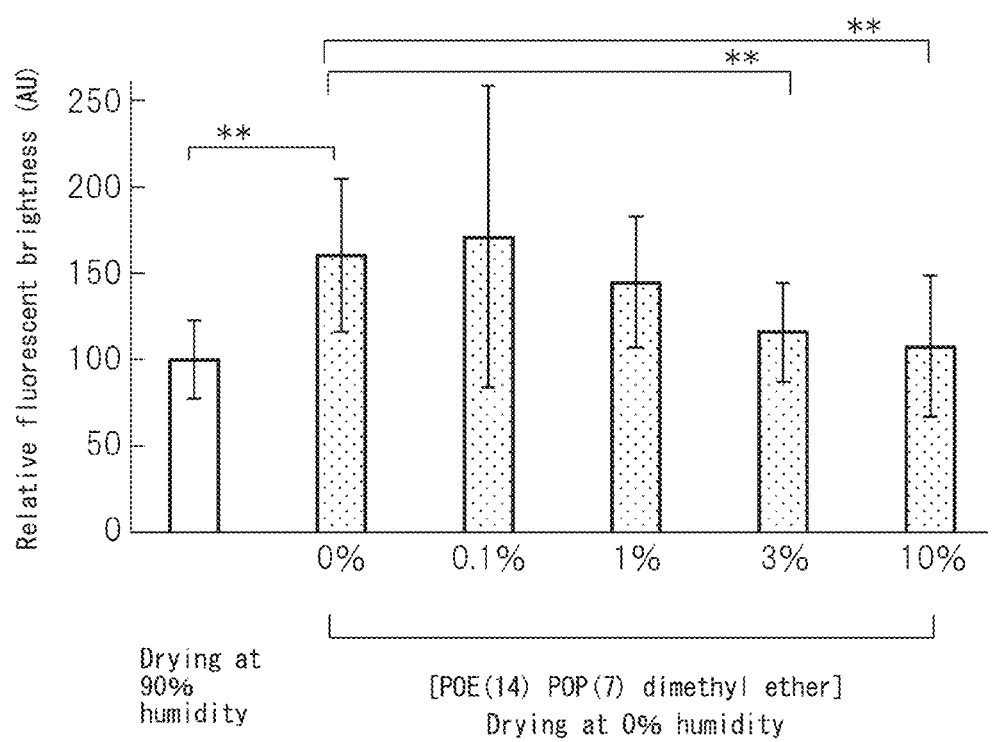
FIG. 7 shows a graph representing fluorescent brightness with fluorescein staining of a stratum corneum sheet after immersion in 0%, 0.1%, 1%, 3% and 10% POE(14) POP(7) dimethyl ether, and then drying at 0% humidity in a sealed container containing silica gel. Drying of a stratum corneum sheet at 90% humidity after immersion in water is shown as 100, for comparison.

Concentration-Dependent Ameliorating Effect on Stratum Corneum by AQUAINPOOL 1407 Aqueous Solution Stratum corneum sheets obtained from the forearm flexor region using stratum corneum release tape were affixed to glass slides, and each affixed stratum corneum sheet was immersed for one hour in water as a control, and in aqueous solutions prepared to AQUAINPOOL 1407 (AQ) concentrations of 0%, 0.1%, 1%, 3% and 10%, as candidate cosmetics. Next, the water-wetted stratum corneum sheet was dried for 2 hours at 90% humidity, room temperature. The AQ-wetted stratum corneum sheet was dried for 2 hours in a sealed container containing silica gel (0% humidity). Each of the stratum corneum sheets was immersed for 5 minutes in a 0.2 w/v % uranin solution (Wako Pure Chemical Industries, Ltd.), and after rinsing, the fluorescent brightness was observed with a fluorescent microscope (BX51 by Olympus Corp.) and an image was taken. The taken image was corrected for distortion and digitized using analysis software, and the fluorescent brightness was calculated. The data for each of 12 visual fields were averaged, and are shown in FIG. 7 with 100 as the fluorescent brightness of a stratum corneum sheet immersed in water and dried at 10% humidity. It was shown that AQUAINPOOL 1407 can lower fluorescent brightness in a concentration-dependent manner, with significant reduction at 3% and 10%, compared to 0% (that is, wetting with water and drying at 0% humidity). Because it lowers fluorescent brightness in a concentration-dependent manner, this demonstrated that AQUAINPOOL 1407 definitely has an ameliorating effect on the stratum corneum, and is useful as a cosmetic with an ameliorating effect on the stratum corneum.

What is claimed is:

1. A method for evaluating stratum corneum condition, comprising:
   contacting a stratum corneum sheet with an aqueous solution of a dye selected from the group consisting of fluorescein, rose bengal and their salts,
   rinsing the dye, and
   measuring the staining intensity of the dye in the stratum corneum sheet.

2. The method according to claim 1, wherein the evaluation of the stratum corneum condition is overall evaluation of stratum corneum transparency, stratum corneum intercellular lipid structure and stratum corneum moisture content.

3. The method according to claim 1, wherein the evaluation is conducted based on comparison with the staining intensity from a prepared sample, or comparison with a color chart.

4. The method according to claim 1, wherein the stratum corneum sheet is a stratum corneum sheet prepared by tape stripping.

5. A method for evaluating a cosmetic treatment in regard to its ameliorating effect on the stratum corneum comprising:
  contacting a stratum corneum sheet, taken by tape stripping after cosmetic treatment of skin, with a dye selected from the group consisting of fluorescein, rose bengal and their salts,
  rinsing the dye, and
  measuring the staining intensity of the dye in the stratum corneum sheet.

6. The method according to claim 5, wherein the evaluation is based on dye staining a stratum corneum sheet obtained by tape stripping before cosmetic treatment, and comparing the staining intensity of the stratum corneum sheet before and after cosmetic treatment.

7. The method according to claim 5, wherein the cosmetic treatment is application of a cosmetic.

8. A method for evaluating a candidate cosmetic in regard to its ameliorating effect on the stratum corneum, comprising:
  applying the candidate cosmetic to a stratum corneum sheet,
  drying the stratum corneum sheet,
  contacting the stratum corneum sheet with an aqueous solution of a dye selected from the group consisting of fluorescein, rose bengal and their salts,
  rinsing the dye, and
  measuring the staining intensity of the dye in the stratum corneum sheet.

9. The method according to claim 8, wherein the stratum corneum sheet is a cultured stratum corneum sheet.

* * * * *